(12) United States Patent
Oldfield et al.

(10) Patent No.: US 7,923,526 B2
(45) Date of Patent: Apr. 12, 2011

(54) SULFOPOLYESTERS HAVING IMPROVED CLARITY IN WATER-DISPERSIBLE FORMULATIONS AND PRODUCTS MADE THEREFROM

(75) Inventors: Terry Ann Oldfield, Kingsport, TN (US); Suzanne Winegar Dobbs, Kingsport, TN (US); Scott Ellery George, Kingsport, TN (US); Ricky Thompson, Kingsport, TN (US); Edward Enns McEntire, Kingsport, TN (US); George William Tindall, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 1145 days.

(21) Appl. No.: 11/193,217

(22) Filed: Jul. 29, 2005

(65) Prior Publication Data

US 2006/0047066 A1     Mar. 2, 2006

Related U.S. Application Data

(60) Provisional application No. 60/606,700, filed on Sep. 1, 2004.

(51) Int. Cl.
*C08G 63/00* (2006.01)

(52) U.S. Cl. ........ 528/279; 528/272; 528/277; 528/293; 528/294; 528/295; 424/47; 424/70.1; 424/70.11; 424/70.24; 424/78.02; 424/78.08; 424/DIG. 1; 424/DIG. 2; 502/100; 502/102; 502/103; 502/150; 502/216; 502/227

(58) Field of Classification Search .................... 424/71, 424/47, 78.02, 70, 45, DIG. 1, DIG. 2, 71.47, 424/70.45, 70.1, 70.11, 70.24, 78.08; 528/272, 528/290, 295, 277, 279, 300, 302, 293; 502/100, 502/102, 103, 150, 216, 227
See application file for complete search history.

(56) References Cited

U.S. PATENT DOCUMENTS

| | | | |
|---|---|---|---|
| 3,734,874 A | 5/1973 | Kibler et al. | |
| 3,779,993 A | 12/1973 | Kibler et al. | |
| 5,158,762 A | 10/1992 | Pierce | |
| 5,266,322 A | 11/1993 | Myers et al. | |
| 5,320,836 A | 6/1994 | Singleton | |
| 5,660,816 A | 8/1997 | Adams et al. | |
| 5,662,893 A | 9/1997 | George et al. | |
| 5,674,479 A | 10/1997 | George et al. | |
| 6,752,983 B1 | 6/2004 | Dobbs et al. | |
| 2004/0024101 A1 * | 2/2004 | Hayes .......................... | 524/445 |

FOREIGN PATENT DOCUMENTS

| | | |
|---|---|---|
| EP | 0551748 A2 | 7/1993 |
| EP | 0861655 A2 | 9/1998 |
| WO | WO 95/00105 | 1/1995 |
| WO | WO 95/33436 | 12/1995 |
| WO | WO 95/33437 | 12/1995 |

OTHER PUBLICATIONS

The International Search Report.

* cited by examiner

*Primary Examiner* — James Seidleck
*Assistant Examiner* — Frances Tischler
(74) *Attorney, Agent, or Firm* — Brett L Nelson; Bernard J. Graves, Jr.

(57) ABSTRACT

A sulfopolyester comprising repeat residue units from the reaction product dimethyl-5-sodiosulfoisophthalate, isophthalic acid, 1,4-cyclohexanedimethanol and diethylene glycol, has at least one property selected from: a) an acidity of greater than 0.030 measured as milliequivalents $H^+$/gram of sulfopolyester; b) a titanium concentration, measured as metal, of less than about 27 ppm, based on the amount of sulfopolyester; or c) an acidity of greater than 0.010 measured as milliequivalents $H^+$/gram of sulfopolyester, a pH of less than 6.0 and a concentration of a base compound of less than 0.0335 moles/kg of sulfopolyester.

A method for making the water-dispersible or water-dissipative sulfopolyester of the present invention is disclosed.

Aqueous dispersion having from 0.001 to about 35 weight % of the sulfopolyester of the present invention is also disclosed. The sulfopolyester is useful in making hair spray formulations suitable for pump or aerosol spray applicators.

3 Claims, No Drawings

US 7,923,526 B2

SULFOPOLYESTERS HAVING IMPROVED CLARITY IN WATER-DISPERSIBLE FORMULATIONS AND PRODUCTS MADE THEREFROM

CROSS REFERENCE TO RELATED APPLICATIONS

Benefit is claimed to the earlier filed application having U.S. Ser. No. 60/606,700 filed Sep. 1, 2004, the entire disclosure of which is incorporated herein by reference.

FIELD OF THE INVENTION

The present invention relates to a water-dispersible or water-dissipative sulfopolyester and products made therefrom. More particularly, one aspect of the present invention relates to a water-dispersible or water-dissipatible, sulfopolyester having greater than about 0.030 hydrogen ion milliequivalents of acid per gram of sulfopolyester (meq $H^+$/g). Another aspect of the present invention is an aqueous dispersion having up to about 35 weight % of the water-dissipatible sulfopolyester dispersed therein wherein the dispersion has an acidity greater than about 0.030 meq $H^+$/g. Yet another aspect of the present invention is a hair spray formulation prepared from the dispersion of the present invention having from about 0.5 weight % to about 35 weight % of a sulfopolyester and having an improved clarity of less than about 20 NTU.

BACKGROUND OF THE INVENTION

Water-dispersible or water-dissipative sulfopolyesters and polyesteramides containing ether groups and sulfonate groups having a glycol residue and a dicarboxylic acid residue and at least one difunctional comonomer containing a sulfonate group attached to an aromatic nucleus and in the form of a metallic salt are well known to those skilled in the art. In particular, such sulfopolyesters can be dissolved, dispersed or otherwise dissipated in aqueous dispersions, preferably at temperatures of less than about 80° C., and have utility in adhesives, coating materials, films, packaging materials, and other products. For example, U.S. Pat. No. 3,734,874 issued to Charles Kibler on May 22, 1973 discloses a sulfopolyester having a glycol component or residue, a dicarboxylic acid component or residue and a difunctional sulfomonomer component. One skilled in the art will understand that the term "residue" or "component" as used in the specification and concluding claims, refers to the moiety that is the resulting product of the chemical species in a particular reaction scheme or subsequent formulation or chemical product, regardless of whether the moiety is actually obtained from the chemical species. Thus, for example, an ethylene glycol residue in a polyester refers to one or more —$OCH_2CH_2O$— repeat units in the polyester, regardless of whether ethylene glycol is used to prepare the polyester.

Sulfopolyesters of particular interest are those requiring particular clarity in a final formulation or use and/or required to retain a particular clarity for a predetermined amount of time afterwards. In this regard, a particularly useful sulfopolyester has an inherent viscosity of 0.24 to 0.60 dl/g. The sulfopolyester has diacid residues comprising from about 20 to 26 mole percent dimethyl-5-sodiosulfoisophthalate and 74 to 80 mole percent isophthalic acid, based on 100 mole percent dicarboxylic acid, and diol residues comprising from about 10 to 30 mole percent 1,4-cyclohexanedimethanol and from about 90 to 70 mole percent diethylene glycol, based on 100 mole percent of the diol. An aqueous dispersion can be made having up to about 35 weight % of the sulfopolyester. However, a problem with such dispersions is that a flocculate or precipitate will form in the aqueous dispersion. In the case where such dispersion is used in the preparation of a hair spray, such flocculate may give the impression that a contaminant is present. It has further been observed that such flocculate may increase the turbidity of the product resulting in clouding of an otherwise clear formulation.

Accordingly, there is a need for a sulfopolyester that is water-dispersible or water-dissipative that is suitable for such hair spray formulations having fast drying times that will have reduced flocculate and have an improved clarity of less than about 20 NTU.

SUMMARY OF THE INVENTION

Briefly, one aspect of the present invention is a water-dispersible or water-dissipative sulfopolyester composition having an inherent viscosity of 0.24 to 0.60 dl/g containing repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol, and wherein the sulfopolyester has at least one property selected from: a) an acidity of greater than 0.030 as measured in milliequivalents $H^+$/gram of sulfopolyester; b) a titanium concentration of less than about 27 ppm, measured as metal, based on the amount of sulfopolyester; or c) an acidity of greater than about 0.010 as measured in milliequivalents $H^+$/gram of sulfopolyester, a pH of less than 6.0, and a concentration of a base added to the sulfopolyester preparation process of less than 0.0335 moles/kg of sulfopolyester; or combinations thereof. The acidity and pH of the sulfopolyester is as measured in a 20 weight % dispersion in demineralized water.

Another aspect of the present invention is a method for making a water-dispersible or water-dissipative sulfopolyester composition having an acidity of greater than 0.030 as measured in milliequivalents $H^+$/gram of sulfopolyester.

Another aspect of the present invention is a method for making a water-dispersible or water-dissipative sulfopolyester composition having a titanium concentration of less than about 27 ppm, based on the amount of sulfopolyester.

Yet another aspect of the present invention is a method for making a water-dispersible or water-dissipative sulfopolyester composition having an acidity of greater than 0.010 as measured in milliequivalents $H^+$/gram of sulfopolyester acidity, a pH of less than 6.0, measured as a 20 weight % sulfopolyester dispersion in demineralized water, and having a base added to the sulfopolyester during the preparation process of less than 0.0335 moles/kg of sulfopolyester.

Another aspect of the present invention is an aqueous dispersion having from about 0.001 weight % to about 35 weight %, and preferably to about 30 weight %, of a sulfopolyester, wherein the sulfopolyester has an inherent viscosity of 0.24 to 0.60 dl/g, and has repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol, and wherein the dispersion includes at least one property selected from: a) an acidity of greater than 0.030 as measured in milliequivalents H$^+$/gram of sulfopolyester; b) a titanium concentration, measured as metal, of less than about 27 ppm based on the amount of sulfopolyester; c) an acidity of greater than 0.010 as measured in milliequivalents H$^+$/gram of sulfopolyester, a pH of less than 6.0, measured as a 20 weight % sulfopolyester dispersion in demineralized water, and a concentration of a base of less than 0.0335 mole/kg of sulfopolyester, wherein the base is added to the sulfopolyester during the preparation process; or combinations thereof. In a preferred embodiment, a 20 weight % dispersion of the sulfopolyester of the present invention has an accelerated flocculation time at 40° C. of greater than 4 hours.

Yet another aspect of the present invention is a hair spray formulation having less than about 20 NTU comprising: (1) from about 0.5 to 12 weight % of a sulfopolyester having an inherent viscosity of 0.24 to 0.60 dl/g containing repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol, and wherein the sulfopolyester has at least one property selected from: a) an acidity of greater than 0.030 as measured in milliequivalents H$^+$/gram of sulfopolyester; b) a titanium concentration of less than about 27 ppm, measured as metal, based on the amount of sulfopolyester; c) an acidity of greater than 0.010 as measured in milliequivalents H$^+$/gram of sulfopolyester, a pH of less than 6.0, measured as a 20 weight % sulfopolyester dispersion in demineralized water, and a concentration of a base added to the sulfopolyester preparation process of less than 0.0335 moles/kg of sulfopolyester; or combinations thereof; and (2) a water/alcohol liquid vehicle wherein the alcohol is an aliphatic straight or branched chain monohydric alcohol having from 2 to 4 carbon atoms.

DETAILED DESCRIPTION OF THE INVENTION

One aspect of the present invention is a water-dispersible or water-dissipative sulfopolyester composition having a glass transition temperature (Tg) of 40° C. to 50° C. and an inherent viscosity of 0.24 to 0.60 dl/g. The inherent viscosity of the sulfopolyester is measured at 23° C. using 0.50 grams of the polymer per 100 ml of a solvent consisting of 60% by weight phenol and 40% by weight tetrachloroethane. The water-dispersible or water-dissipative sulfopolyester contains repeat units from a difunctional sulfomonomer, at least one dicarboxylic acid, and at least one diol. The sulfopolyester contains about 20 to about 26 mole percent of dimethyl-5-sodiosulfoisophthalate and about 74 to about 80 mole percent isophthalic acid, based on 100 mole percent of the difunctional sulfomonomer and dicarboxylic acid. The diol component of the sulfopolyester contains about 10 to about 30 mole percent 1,4-cyclohexanedimethanol and about 90 to about 70 mole percent diethylene glycol, based on 100 mole percent diol. The sulfopolyester of the present composition should have at least one property selected from: a) an acidity of greater than 0.030 as measured in milliequivalents H$^+$/gram of sulfopolyester; b) a titanium concentration of less than about 27 ppm, measured as metal, based on the amount of sulfopolyester; or c) an acidity of greater than 0.010 as measured in milliequivalents H$^+$/gram of sulfopolyester, a pH of less than 6.0, measured as a 20 weight % sulfopolyester dispersion in demineralized water, and a concentration of a base, as added to the sulfopolyester preparation process, of less than 0.0335 moles/kg of sulfopolyester. One skilled in the art would understand that the term "at least one property" means the sulfopolyester can have combinations of the aforementioned properties (a)-(c). Advantageously, it has unexpectedly been discovered that aqueous dispersions can be prepared from the sulfopolyester of the present invention which have flocculation times, as determined by the rapid floc method, of greater than about 4 hours.

The general reaction conditions for preparing a water-dispersible or water-dissipative sulfopolyester having an inherent viscosity of 0.24 to 0.60 dl/g containing repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol are described in U.S. Pat. No. 5,660,816, the entire disclosure of which is incorporated herein by reference. Water-dispersible or water-dissipative sulfopolyester compositions are available from Eastman Chemical Company, Kingsport, Tenn. under the trade name of EASTMAN AQ®48.

In preparing the water-dispersible or water-dissipative sulfopolyester of the present invention having the above dicarboxylic acid and diol constituents and having an acidity of greater than 0.030 as measured in milliequivalents H$^+$/gram of sulfopolyester, the general reaction conditions described in U.S. Pat. No. 5,660,816 are followed with the following exception. A predetermined amount of a pH-lowering composition or compound is added during at least one step of the of the polymer process which includes the steps of: 1) initial mixing of the reactants; 2) esterification or transesterification of the reactants to make an oligomer or monomer; and 3) polycondensation of the ester monomer. It is to be understood that the term "at least one step" would include adding the pH-lowering compound or composition to any combination of steps during the process. The amount of pH-lowering compound or composition added to the process during any one of these steps is easily determined by one skilled in the art and is dependent upon the type and concentration of the pH-lowering compound or composition. Preferably, the pH-lowering compound or composition is added during step (1), i.e., at the initial mixing of the reactants and prior to esterification or transesterification.

Suitable pH-lowering compounds or compositions are capable of decreasing the pH, as measured in a 20 weight % sulfopolyester dispersion in demineralized water and include HCl, HBr, HI, HClO$_4$, H$_2$SO$_4$, HNO$_3$, sulfonic acids, sulfurous acid, sodium hydrogen sulfate, sodium sulfate, and mixtures thereof. Preferred pH-lowering compounds or compositions include sodium hydrogen sulfate, H$_2$SO$_4$, sodium sulfate, and mixtures thereof. The added acid may have a concentration of from about 3 to about 100 weight %, preferably from about 3 to about 40 weight %, more preferably from about 5 to about 20 weight %, and most preferably from about 5 to about 10 weight %. However, one skilled in the art would understand that the concentration of pH-lowering compounds or compositions is secondary and may be any concentration to achieve the desired acidity and/or pH of dispersion prepared from the sulfopolyester.

Desirably, the acidity of the sulfopolyester prepared by the above process, measured in milliequivalents H$^+$/gram of sulfopolyester, is from 0.030 to about 0.060, preferably from about 0.030 to about 0.055, and more preferably from about 0.030 to about 0.045, and most preferably from about 0.030 to about 0.040. The acidity of the sulfopolyester, measured in milliequivalents $H^+$/gram of sulfopolyester, is determined by first dispersing the sulfopolyester in water. The dispersion can contain about 5 to 35 weight % of the sulfopolyester, and preferably contains from about 20 to 30 weight % of the sulfopolyester. The dispersion is made by heating the water to about 40° to 50° C. and adding the sulfopolyester with rapid stirring and maintaining the temperature in this range until the sulfopolyester is dispersed in the water. After cooling to room temperature, the sulfopolyester dispersion is titrated with a known normality of 0.05 to 0.1 sodium hydroxide in water, and preferably using a 0.05 N solution. The endpoint of the titration is determined potentiometrically.

Another aspect of the present invention is the composition and method for making the water-dispersible or water-dissipative sulfopolyester having an inherent viscosity of 0.24 to 0.60 dl/g containing repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol and having a titanium concentration, measured as metal, of less than about 27 ppm, based on the amount of sulfopolyester. The general process conditions for making the sulfopolyester composition having a titanium concentration of less than about 27 ppm, based on the amount of sulfopolyester, is described in U.S. Pat. No. 5,660,816, with the following exception. The amount of titanium, measured as metal, added to the reactants and present in the resulting sulfopolyester product is less than about 27 parts per million (ppm), based on the amount of sulfopolyester. Desirably, the amount of titanium, measured as metal, added to the reactants and present in the resulting sulfopolyester product is from about 5 ppm to about 27 ppm, and more preferably from about 15 ppm to about 25 ppm.

Another aspect of the present invention is the composition and method for making a sulfopolyester having an inherent viscosity of 0.24 to 0.60 dl/g containing repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol and having an acidity of greater than 0.010 as measured in milliequivalents $H^+$/gram of sulfopolyester, a pH of less than 6.0, measured as a 20 weight % sulfopolyester dispersion in demineralized water, and a concentration of a base added to the sulfopolyester preparation process of less than 0.0335 equivalents/kg of sulfopolyester. Suitable bases include, but are not limited to, sodium acetate, sodium hydroxide, potassium hydroxide, and mixtures thereof. The general process for making the sulfopolyester of the present invention is described in U.S. Pat. No. 5,660,816 with the following exceptions: 1) an amount of pH-lowering compound may optionally be added during at least one step of the process, which generally includes the steps of: a) initial mixing of the reactants; b) esterification or transesterification of the reactants to make an oligomer or monomer; and c) polycondensation of the ester monomer; and 2) an amount of base added to the sulfopolyester preparation process is less than 0.0335 equivalents/kg of sulfopolyester.

Preferably, the acidity of the sulfopolyester ranges from about 0.010 to about 0.085, and more preferably from about 0.019 to about 0.060, and most preferably from about 0.019 to about 0.040 measured in milliequivalents $H^+$/gram of sulfopolyester. The acidity of the sulfopolyester is measured in a 20 weight % sulfopolyester dispersion in demineralized water.

Preferably, the pH of the sulfopolyester ranges from about 3.0 to less than 6.0, more preferably, from about 3.5 to about 5.95, and most preferably from about 3.8 to about 5.95. The pH of the sulfopolyester is measured in a 20 weight % sulfopolyester dispersion in demineralized water.

The amount of base compound added to the sulfopolyester preparation process is less than about 0.0335 equivalents/kg of sulfopolyester, preferably is less than about 0.0258 equivalents/kg of sulfopolyester, and more preferably less than about 0.0200, and most preferably is less than about 0.010 equivalents of base compound/kg of sulfopolyester. It is to be understood that the above concentration ranges of the pH-lowering compound, pH and amount of base compound added to the sulfopolyester include all ranges and concentrations between those explicitly enumerated. Moreover, it is to be understood that the acidity, pH and amount of base compound added to the sulfopolyester may be independently adjusted within their respective ranges or concentrations.

A desirable sulfopolyester composition has an acidity of from about 0.010 to about 0.085 milliequivalents $H^+$/gram of sulfopolyester, pH is from about 3.0 to about 6.0 and the concentration of the base compound is less than about 0.0258 equivalents/kg of sulfopolyester. More desirably, the sulfopolyester composition has an acidity of from about 0.019 to about 0.060 milliequivalents $H^+$/gram of sulfopolyester, a pH from about 3.5 to about 5.95, and the concentration of the base compound of less than about 0.0200 equivalents/kg of sulfopolyester. Most desirably the sulfopolyester composition has an acidity of from about 0.019 to about 0.040 milliequivalents $H^+$/gram of sulfopolyester, a pH from about 3.8 to about 5.95, and the concentration of the base compound is less than about 0.0100 equivalents/kg of sulfopolyester, wherein the acidity and pH of the sulfopolyester are measured in a 20 weight % sulfopolyester dispersion in demineralized water and the amount of base compound added is to the sulfopolyester preparation process.

Another aspect of the present invention is an aqueous dispersion having from about 0.001 weight % up to about 35 weight % of a sulfopolyester of the present invention wherein the aqueous dispersion has at least one property selected from: 1) an acidity of greater than 0.030 as measured in milliequivalents $H^+$/gram of sulfopolyester; 2) a titanium concentration, measured as metal, of less than about 27 ppm, based on the amount of sulfopolyester; 3) an acidity of greater than 0.010 as measured in milliequivalents $H^+$/gram of sulfopolyester, a pH less than 6.0, measured as a 20 weight % sulfopolyester dispersion in demineralized water, and a concentration of a base compound added to the sulfopolyester preparation process of less than 0.0335 equivalents/kg of sulfopolyester. Advantageously, the aqueous dispersion(s) of the present invention have a flocculation time, as determined by the rapid floc method, of greater than about 4 hours, and preferably greater than about 7 hours.

In preparing the aqueous dispersions of the present invention, a predetermined amount of the sulfopolyester composition of the present invention is mixed with water to produce an aqueous dispersion having from 0.001 weight % to about 35 weight % of the sulfopolyester. More specifically, the water-dispersible or water-dissipative sulfopolyester composition(s) of the present invention having at least one property selected from: a) an acidity of greater than 0.030 as measured in milliequivalents H$^+$/gram of sulfopolyester; b) a titanium concentration of less than about 27 ppm, measured as metal, based on the amount of sulfopolyester; or c) an acidity of greater than 0.010 as measured in milliequivalents H$^+$/gram of sulfopolyester, a pH less than 6.0, measured as a 20 weight % sulfopolyester dispersion in demineralized water, and a concentration of a base compound added to the sulfopolyester preparation process of less than 0.0335 equivalents/kg of sulfopolyester described above are used in making the aqueous dispersion(s) having the respective at least one property of: 1) an acidity of greater than 0.030 as measured in milliequivalents H$^+$/gram of sulfopolyester; 2) a titanium concentration, measured as metal, of less than about 27 ppm, based on the amount of sulfopolyester; 3) an acidity of greater than 0.010 as measured in milliequivalents H$^+$/gram of sulfopolyester, a pH less than 6.0 measured as a 20 weight % sulfopolyester dispersion in demineralized water, and has a concentration of a base compound of less than 0.0335 equivalents/kg of sulfopolyester added to the sulfopolyester preparation process. Accordingly, for the sake of brevity, the aqueous dispersions prepared from the respective sulfopolyesters described above also includes dispersions having: 1) preferred acid concentrations of from 0.030 to about 0.060 milliequivalents H$^+$/gram of sulfopolyester, more preferred acid concentrations of from 0.030 to about 0.055 milliequivalents H$^+$/gram of sulfopolyester, and most preferred acid concentrations of from 0.030 to about 0.045 milliequivalents H$^+$/gram of sulfopolyester; 2) preferred titanium concentrations, measured as metal, of from 5 to 27 ppm, and more preferred titanium concentrations from 15 to 25 ppm, based on the amount of sulfopolyester; and/or 3) i) a preferred acidity from 0.010 to about 0.085 milliequivalents H$^+$/gram of sulfopolyester, a pH of from about 3.0 to about 6.0, and a base compound of less than 0.0258 equivalents/kg of sulfopolyester, ii) a more preferred acidity of 0.019 to about 0.060 milliequivalents H$^+$/gram of sulfopolyester, a pH of from about 3.5 to about 5.95 and a base compound of less than 0.020 equivalents/kg of sulfopolyester, and iii) a most preferred acidity of 0.019 to about 0.040 milliequivalents H$^+$/gram of sulfopolyester, a pH of from about 3.8 to about 5.95 and a base compound of less than 0.010 equivalents/kg of sulfopolyester, wherein the acidity and pH are measured as a 20% sulfopolyester dispersion in demineralized water and the base is as added to the sulfopolyester during preparation process. In a preferred embodiment the base is sodium acetate.

Desirably, the water is a demineralized water, such as distilled or deionized water, having a temperature of from about 30° C. to about 60° C. Preferably, the water has a temperature of from about 40° C. to about 55° C., more preferably from about 40° C. to about 50° C., and most preferably from about 40° C. to about 45° C.

Another method for preparing the sulfopolyester aqueous dispersions having an acidity of greater than 0.030 as measured in milliequivalents H$^+$/gram of sulfopolyester includes the steps of providing a predetermined amount of the sulfopolyester EASTMAN AQ948 available from Eastman Chemical Company; mixing a predetermined amount of water with a predetermined amount of acid to form an acid solution; and adding the sulfopolyester to the acid solution to produce an aqueous dispersion having up to about 35 weight % of the sulfopolyester to produce a dispersion having acidity to greater than 0.030 as measured in milliequivalents H$^+$/gram of sulfopolyester. Desirably, the acid added to prepare the 35 weight % aqueous dispersion is selected from the group consisting of HCl, HBr, HI, HClO$_4$, H$_2$SO$_4$, HNO$_3$, sodium hydrogen sulfate, sulfonic, acetic, phosphoric, phosphorous, sulfurous, trichloroacetic, salicylic, phthalic, nitrous, lactic, iodic, formic, citric, tartaric, and chloroacetic. Preferred acids are HCl, sodium hydrogen sulfate, H$_2$SO$_4$, phosphoric, acetic, salicylic, lactic, formic, tartaric, and citric. More preferably, the acid added to the aqueous dispersion is selected from sodium hydrogen sulfate, sulfuric acid and mixtures thereof.

Another aspect of the present invention is a hair spray formulation having less than about 20 NTU comprising from about 0.5 to 95 weight %, preferably from about 1.0 to about 60 weight %, more preferably from about 1.0 to about 45 weight %, and most preferably from about 5 to about 40 weight % of the sulfopolyester aqueous dispersion(s) of the present invention and a water/alcohol liquid vehicle having up to about 55 weight % of alcohol and wherein the alcohol is an aliphatic straight or branched chain monohydric alcohol having from 2 to 4 carbon atoms, wherein the weight percent is based on the total weight of constituents in the hair spray formulation.

Distilled or deionized water are the preferred sources of water since tap water generally contains ions that may precipitate the sulfopolyester component. Preferably a water/alcohol mixture is used wherein the alcohol is present in an amount less than about 55 weight % based on the weight of the hair spray formulation. The alcohol provides faster drying of the formulation on hair as compared to formulations prepared with only water as the liquid vehicle. The alcohol is an aliphatic straight or branched chain monohydric alcohol having 2 to 4 carbon atoms. Isopropanol and ethanol are the preferred alcohols. However, if additional ingredients are used in the pump hair spray formulation, the amount of the liquid vehicle will be proportionally reduced.

For example, the hair spray formulation may further contain from 0.5 to 10 weight % of a water-soluble, water-dispersible, water/alcohol-soluble, or water/alcohol-dispersible polymer or co-resin. One skilled in the art will recognize that some acidic co-resins require neutralization with a base, such as aminomethylpropanol, to become soluble in water-alcohol blends. The term "water-soluble" refers to any material that has solubility of at least 1 gram per 100 grams of water, i.e. 1%, preferably a solubility of at least 5% by weight and must be soluble or otherwise dispersible in the liquid vehicle. Conversely, the term "water-insoluble" refers to substances that are insoluble at a level of less than 1 gram per 100 grams of water, i.e., less than 1% by weight. Solubility or dispersibility is determined at ambient conditions (e.g., a temperature of about 25° C. and atmospheric pressure). Preferably, the water-soluble, or water/alcohol-soluble polymer or co-resin has a weight average molecular weight of from about 1,000 to 2,000,000 and is prepared from at least one vinyl monomer selected from the group consisting of alkyl vinyl ethers, alkyl acrylates, vinyl esters, n-vinyl lactams, alkyl acrylamides, half vinyl esters/half amides, half esters of maleic anhydride vinyl pyrrolidone, acrylic acid, crotonic acid, methacrylic acid, and esters of acrylic acid, crotonic acid and methacrylic acid, and mixtures thereof. The water-soluble polymer or resin is described in greater detail in U.S. Pat. No. 5,662,893, the disclosure of which is incorporated herein by reference. The preferred water/alcohol-soluble or water/alcohol-dispersible polymers include octylacrylamide/acrylates/butylaminoethyl methacrylate copolymer neutralized with a base such as aminomethylpropanol. The water-soluble, water/alcohol-soluble or water/alcohol-dispersible polymers are used at a level of from about 0.5% to about 10% by weight, generally about 0.5% to about 5% by weight, and preferably from 0.5% to 4% by weight of the total formulation. The weight average molecular weight of the polymers is not critical but is generally in the range from about 1,000 to 2,000,000.

When the hair spray formulation is used in the form of an aerosol spray, the aerosol formulation will include a propellant. The propellant may be any liquefiable gas conventionally used for aerosols. Examples of materials that are suitable for use as propellants are chlorodifluoromethane, 1,1-difluoroethane, monochlorodifluoromethane, dimethyl ether, $C_1$-$C_4$ hydrocarbons such as methane, ethane, propane, n-butane, and isobutane, and mixtures thereof. Water-soluble gases such as dimethyl ether, carbon dioxide, and/or nitrous oxide also may be used to obtain aerosols having reduced flammability. Preferably, the propellant is a 1,1-difluoroethane, dimethyl ether, or combinations thereof. The amount of propellant typically is from about 10 to 55 weight percent, preferably from about 20 to 45 weight percent, based on the total weight of the composition. However, the total amount of propellant and alcohol should not exceed 55 weight %.

The hair spray formulation may also contain a variety of other optional components suitable for rendering such formulations more acceptable. Such conventional optional ingredients are well known to those skilled in the art. For example, the hair-spray formulation of the present invention may also include from about 0.01 to 3 weight %, preferably from 0.1 to 1 weight % of a non-volatile silicone compound or other conditioning agent(s); preferably a water-insoluble, emulsifiable conditioning agent. The preferred non-volatile silicone compound is dimethicone copolyol. The non-volatile dimethicone copolyol is added to the formulation of the present invention in an amount sufficient to provide good spreading of the hairspray droplets on the hair and improved comb out.

The aqueous formulations of the present invention also can contain the conventional hair spray adjuvants in amounts which generally range from about 0.01 to 2% by weight and preferably 0.1% to 1% by weight. Among the additives which can be used are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

The present invention is illustrated in greater detail by the specific examples presented below. It is to be understood that these examples are illustrative embodiments and are not intended to be limiting of the invention, but rather are to be construed broadly within the scope and content of the appended claims. All parts and percentages in the examples are on a weight basis unless otherwise stated.

Example 1

A sulfopolyester in accordance with the present invention was prepared by adding 1,4 cyclohexanedimethanol, diethylene glycol, 5-sodiosulfoisophthalic acid and isophthalic acid to a vessel and agitated to provide a uniform blend. Sodium acetate was added to the blend at a ratio of 0.0036 pound per pound of sulfopolyester (0.043 moles of sodium acetate/kg of sulfopolyester) (theoretical yield). An amount of 8% sulfuric acid was added to the blend to provide 0.00435 meq $H^+$/g sulfopolyester based on theoretical yield. An amount of titanium (IV) isopropoxide (equivalent 50 ppm Ti metal based on the weight of the sulfopolyester) was added to the vessel as a catalyst. Transesterification was performed under nitrogen atmosphere and at a temperature of from about 210° to 230° C. over a period of about 4 hours. Polycondensation was performed at 2 mm of Hg at 270° C. for several hours. The addition of the acid did not cause any charring as evidenced by the absence of black particulate matter in the sulfopolyester.

Comparative Example 2

A sulfopolyester was prepared as described in Example 1 above, except that no additional sulfuric acid was added to the sulfopolyester. Color data of the sulfopolyester is provided in Table 1 below.

TABLE 1

| Example No. | Color | | |
|---|---|---|---|
| | L* | a* | b* |
| 1 | 67.17 | −0.07 | 12.31 |
| Comp. 2 | 64.57 | 0.02 | 12.66 |

Comparative Examples 3 & 4

Selected samples of a sulfopolyester produced by the method of Example 2 above were dispersed in water heated to 44° C. and 54° C. to prepare dispersions having a 30 weight % concentration of sulfopolyester. The acidity of the dispersions prepared at 44° C. was measured by titration using sodium hydroxide solution. Each sulfopolyester dispersion was stored at room temperature and observed each day to determine the time for flocculation to occur. In addition, each dispersion was used the same day it was prepared to make a hydroalcoholic solution containing 5 weight % sulfopolyester and 55 weight % ethanol. The turbidity of this dispersion was measured in NTU using a Hach 2100N IS Laboratory Turbidimeter using the procedure provided by the instrument manufacturer. The results are shown in Table 2 below.

TABLE 2

| Example No. | 30% AQ Sulfopolyester in water | | | 5% AQ, 55% Ethanol mixture Turbidity (NTU) | |
|---|---|---|---|---|---|
| | Acidity (meq/g) | Time to floc (days) | | | |
| | 44° C. | 44° C. | 54° C. | 44° C. | 54° C. |
| 3 | 0.015 | 6 | 0 | 11 | 28* |
| 4 | 0.014 | 5 | 0 | 17 | 30* |

*Contains precipitate.

Examples 5-16

For Examples 5-14, selected samples of a sulfopolyester produced by the method of Example 1 above were dispersed in water heated to 44° C. and 54° C. to prepare dispersions having a 30 weight % concentration of sulfopolyester. For Examples 15 and 16, the sulfopolyester was produced by the method of Example 1, except the amount of 8% sulfuric acid added was 0.0210 meq $H^+$/g sulfopolyester. The acidity of the dispersions prepared at 44° C. was measured by titration using sodium hydroxide solution. Each dispersion was observed to determine the amount of time for flocculation to occur. In addition, each dispersion was used the same day that it was prepared to make a hydroalcoholic dispersion containing 5 weight % sulfopolyester and 55 weight % ethanol. The results are shown in Table 3 below.

TABLE 3

| Example No. | Acidity (meq/g) | 30% AQ Sulfopolyester in water | | 5% AQ, 55% Ethanol mixture Turbidity (NTU) | |
|---|---|---|---|---|---|
| | | Time to floc (days) | | | |
| | 44° C. | 44° C. | 54° C. | 44° C. | 54° C. |
| 5  | 0.018 | 20   | 5   | 5  | 34  |
| 6  | 0.019 | 24   | 8   | 5  | 11  |
| 7  | 0.020 | 30   | 5   | 5  | 37  |
| 8  | 0.019 | 22   | 3   | 5  | 44  |
| 9  | 0.018 | 18   | 3   | 6  | 46  |
| 10 | 0.020 | 40   | 12  | 5  | 8   |
| 11 | 0.017 | 12   | 0   | 6  | 43* |
| 12 | 0.017 | 11   | 0   | 6  | 23* |
| 13 | 0.017 | 13   | 0   | 6  | 23* |
| 14 | 0.017 | 13   | 2   | 7  | 79  |
| 15 | 0.049 | >140 | >31 | 13 | 23  |
| 16 | 0.039 | >132 | >31 | 11 | 16  |

*Contains precipitate.

These results show the benefit of preparing a sulfopolyester or dispersion of a sulfopolyester having acidity greater than 0.030 meq $H^+$/gram of sulfopolyester particularly in a hair spray formulation. Accordingly, adding acid to the sulfopolyester during production or otherwise increasing the acidity of the sulfopolyester, or increasing the acidity of the dispersion increases the time for flocculation to occur.

Example 17

An aerosol hairspray formulation was prepared as follows. Aminomethylpropanol (0.27 g, AMP-95) was added to 30.8 g anhydrous SDA-40B (Specially Denatured Alcohol) and mixed. Balance 47, a resin from National Starch (1.53 g), was added slowly with stirring and mixed until dissolved. In a separate container, 20.6 g of the sulfopolyester/water dispersion of Example 15 prepared at 54° C. was diluted with 46.9 g water. The Balance 47/alcohol solution was then added to the sulfopolyester dispersion with stirring. This mixture (29.0 g) was mixed with 23.6 ml dimethyl ether propellant in a glass aerosol container. The aerosol hairspray was clear and contained no precipitate

Examples 18-58

In the following examples, the floc times were determined using the accelerated floc method. In evaluating the sulfopolyester and dispersions using the accelerated floc method, dispersions having a 20 weight % concentration of sulfopolyester were prepared by dispersing an amount of a sulfopolyester, with rapid stirring, in water heated to about 42° C. The 20% concentration was chosen because floc forms faster at a 20% concentration versus a dispersion having higher concentration of sulfopolyester. About 50 mL of the 20% sulfopolyester aqueous dispersions were then poured into vials having about one-half of an inch (1.27 cm) diameter. The vials were capped and placed in an oven at 40° C. The samples were then observed every 30 minutes to determine the time for flocculation to occur.

In the following examples, sulfopolyesters were prepared as described in Example 1 except different amounts of the pH lowering compound, i.e., acid, titanium (as metal), and sodium acetate (base) were added. Each sample had the concentrations of: titanium, as metal; sodium acetate added; and the measured acidity levels and pH as specified in Table 4. Dispersions having a 20 weight % concentration of the respective sulfopolyesters were prepared and the flocculation time for each was determined in accordance with the accelerated floc method described above. The results appear in Table 4 below.

TABLE 4

| Example No. | Ti[1] | NaOAc[2] | Acidity[3] | pH | Floc time[4] hrs. |
|---|---|---|---|---|---|
| 18 | 50 | 0.0335 | 0.010  | 6.13 | 2.0 |
| 19 | 50 | 0.0335 | 0.010  | 6.10 | 2.0 |
| 20 | 40 | 0.0335 | 0.011  | 6.09 | 2.5 |
| 21 | 39 | 0.0335 | 0.010  | 6.12 | 2.5 |
| 22 | 29 | 0.0335 | 0.0120 | 6.03 | 3.0 |
| 23 | 27 | 0.0335 | 0.0115 | 6.01 | 3.5-4.0 |
| 24 | 23 | 0.0335 | 0.0135 | 5.99 | 6.5 |
| 25 | 20 | 0.0335 | 0.0125 | 5.94 | 6.5 |
| 26 | 20 | 0.0258 | 0.0125 | 5.96 | 6.5 |
| 27 | 20 | 0.0258 | 0.0115 | 5.91 | 6.5 |
| 28 | 20 | 0.0258 | 0.0115 | 5.91 | 6.0 |
| 29 | 20 | 0.0258 | 0.0115 | 5.92 | 6.5 |
| 30 | 20 | 0.0258 | 0.0188 | 5.89 | 7.0 |
| 31 | 15 | 0.0258 | 0.0366 | 5.5  | >42.5 |
| 32 | 14 | 0.0258 | 0.0321 | 5.55 | 26-28 |
| 33 | 21 | 0.0258 | 0.0185 | 6.03 | 4.0 |
| 34 | 25 | 0.0335 | 0.0205 | 6.05 | 7.5-8.0 |
| 35 | 50 | 0      | 0.0145 | 5.73 | 7.0 |
| 36 | 50 | 0      | 0.0155 | 5.63 | 38.5-80 |
| 37 | 50 | 0      | 0.0290 | 3.84 | >1352 |
| 38 | 50 | 0.0335 | 0.0130 | 6.17 | 3.0 |
| 39 | 50 | 0.0335 | 0.0115 | 5.71 | 3.5 |
| 40 | 25 | 0      | 0.0200 | 5.51 | >84.5 |
| 41 | 50 | 0      | 0.0165 | 5.85 | 43.5 |
| 42 | 25 | 0      | 0.0105 | 5.59 | >69 |
| 43 | 50 | 0.067  | 0.0300 | 6.05 | 7.5 |
| 44 | 50 | 0.0335 | 0.0220 | 5.83 | 4.5 |
| 45 | 50 | 0.0335 | 0.0160 | 6.13 | 1.5 |
| 46 | 50 | 0.0335 | 0.0181 | 5.96 | 3.0 |
| 47 | 50 | 0.0335 | 0.0193 | 5.87 | 3.5 |
| 48 | 50 | 0.0335 | 0.0155 | 5.98 | 2.5 |
| 49 | 50 | 0.0335 | 0.0135 | 5.96 | 2.5 |
| 50 | 50 | 0.0335 | 0.0155 | 5.49 | 6 |
| 51 | 50 | 0.0335 | 0.0160 | 5.33 | 14 |
| 52 | 50 | 0.0335 | 0.0195 | 5.20 | >1664 |
| 53 | 11 | 0      | 0.0715 | 4.71 | >120 |
| 54 | 12 | 0.0122 | 0.0415 | 5.33 | >120 |
| 55 | 24 | 0      | 0.0325 | 5.11 | >103.5 |
| 56 | 14 | 0.0146 | 0.0345 | 5.38 | >24 |
| 57 | 27 | 0.0146 | 0.0330 | 5.44 | >24 |
| 58 | 23 | 0.0122 | 0.0310 | 5.38 | >24 |

[1]parts per million Ti based on the sulfopolyester.
[2]equivalents of sodium acetate per kg of sulfopolyester.
[3]acidity as measured in milliequivalents per gram sulfopolyester.
[4]based on a 20 weight % dispersion prepared using the respective sulfopolyester.

Examples 59-73

In the following Examples, the sulfopolyesters of Examples 34-42 and 53-58, respectively, were formulated to a solution having 5 weight % of the specified sulfopolyester and 55 weight % ethanol. The turbidity, measured in NTU, for the solutions is given in Table 5 below.

TABLE 5

| | Turbidity NTU | |
|---|---|---|
| Example No. | After 1 day | After 1 week |
| 59 | 14 | 11 |
| 60 | 15 | 13 |
| 61 | 18 | 12 |
| 62 | 9  | 8  |
| 63 | 16 | 14 |
| 64 | 14 | 14 |
| 65 | 13 | 9  |
| 66 | 23 | 17 |

TABLE 5-continued

| Example No. | Turbidity NTU | |
| --- | --- | --- |
| | After 1 day | After 1 week |
| 67 | — | 8 |
| 68 | 7 | 10 |
| 69 | 6 | 6 |
| 70 | 6 | 6 |
| 71 | 7 | — |
| 72 | 7 | — |
| 73 | 11 | — |

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

We claim:

1. A water-dispersible or water-dissipative sulfopolyester having an inherent viscosity of 0.24 to 0.60 dl/g comprising repeat residue units of the reaction product of about 20 to about 26 mole percent dimethyl-5-sodiosulfoisophthalate and about 74 to about 80 mole percent isophthalic acid, based on 100 mole percent of the dimethyl-5-sodiosulfoisophthalate and isophthalic acid, and about 10 to about 30 mole percent 1,4-cyclohexanedimethanol and about 90 to about 70 mole percent diethylene glycol, based on 100 mole percent of the 1,4-cyclohexanedimethanol and diethylene glycol, and wherein the sulfopolyester has a titanium concentration of less than about 27 ppm, measured as metal, based on the amount of sulfopolyester.

2. The sulfopolyester of claim 1 wherein said titanium concentration is from about 5 to about 27 ppm, measured as metal, based on the amount of sulfopolyester.

3. The sulfopolyester of claim 2 wherein said titanium concentration is from about 15 to about 25 ppm, measured as metal, based on the amount of sulfopolyester.

* * * * *